(12) United States Patent
Zhang et al.

(10) Patent No.: US 7,930,020 B2
(45) Date of Patent: Apr. 19, 2011

(54) MORPHOLOGY BASED ARRHYTHMIA DETECTION

(75) Inventors: Xin Zhang, New Brighton, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 995 days.

(21) Appl. No.: 11/741,057

(22) Filed: Apr. 27, 2007

(65) Prior Publication Data

US 2008/0269624 A1    Oct. 30, 2008

(51) Int. Cl.
*A61B 5/0472* (2006.01)

(52) U.S. Cl. ...................................................... 600/515

(58) Field of Classification Search .................... 600/515
See application file for complete search history.

(56) References Cited

U.S. PATENT DOCUMENTS

| | | | |
|---|---|---|---|
| 4,184,493 A | 1/1980 | Heilman et al. | |
| 4,905,708 A | 3/1990 | Davies | |
| 5,117,824 A | 6/1992 | Keimel et al. | |
| 5,400,795 A * | 3/1995 | Murphy et al. | 600/515 |
| 6,212,428 B1 | 4/2001 | Hsu et al. | |
| 6,393,316 B1 * | 5/2002 | Gillberg et al. | 600/515 |
| 6,522,915 B1 | 2/2003 | Ceballos et al. | |
| 6,731,978 B2 | 5/2004 | Olson et al. | |
| 6,980,860 B2 | 12/2005 | Stadler et al. | |
| 7,039,463 B2 | 5/2006 | Marcovecchio et al. | |
| 7,130,677 B2 | 10/2006 | Brown et al. | |
| 2003/0144700 A1 | 7/2003 | Brown et al. | |
| 2004/0093035 A1 | 5/2004 | Schwartz et al. | |
| 2005/0065444 A1 | 3/2005 | Erkkila | |
| 2005/0137485 A1 | 6/2005 | Cao et al. | |
| 2006/0161069 A1 | 7/2006 | Li et al. | |
| 2007/0232948 A1 * | 10/2007 | Stadler et al. | 600/512 |

OTHER PUBLICATIONS

Tooley M A et al: "Recognition of multiple tachyarrhythmias by rate-independent means using a small microcomputer." PACE, vol. 14, No. 2, Feb. 1991, pp. 337-340, XP002488774.
International Search Report, PCT/US2008/059699, Jan. 8, 2008, 6 Pages.

* cited by examiner

*Primary Examiner* — Eric D. Bertram
(74) *Attorney, Agent, or Firm* — Michael C. Soldner

(57) ABSTRACT

A medical device system and associated method sample an EGM signal over a processing window having a predetermined time duration. A number of morphology metrics are determined from the sampled EGM signal, and a heart rhythm is detected in response to the morphology metrics without determining depolarization intervals. The morphology metrics include metrics determined from a slope signal derived from the EGM signal in one embodiment.

23 Claims, 8 Drawing Sheets

MORPHOLOGY BASED ARRHYTHMIA DETECTION

TECHNICAL FIELD

The invention relates generally to medical devices and, in particular, to a method for detecting heart rhythms using a cardiac electrogram (EGM) morphology-based algorithm.

BACKGROUND

Implantable medical devices are available for treating cardiac arrhythmias by delivering anti-tachycardia pacing therapies and electrical shock therapies for cardioverting or defibrillating the heart. Such a device, commonly known as an implantable cardioverter defibrillator or "ICD", conventionally senses a patient's heart rate and classifies the rate according to a number of heart rate zones in order to detect episodes of tachycardia or fibrillation. Atrial and ventricular arrhythmias are typically detected by initially identifying a fast atrial and/or ventricular rate based on measuring the time intervals between sensed atrial depolarizations or "P-waves" and/or sensed ventricular depolarizations or "R-waves".

Typically a number of predefined rate zones are defined according to programmable detection interval ranges for detecting slow tachycardia, fast tachycardia and fibrillation. Sensed event intervals falling into defined detection interval ranges are counted to provide a count of tachycardia intervals. A programmable number of intervals to detect (NID) defines the number of tachycardia intervals occurring consecutively or out of a given number of preceding event intervals that are required to detect tachycardia. A separately programmed NID may be defined for detecting slow and fast tachycardia and fibrillation.

Once a tachycardia is detected based on sensed P-wave or R-wave intervals, the morphology of the sensed depolarization signals may be used in discriminating heart rhythms to improve the sensitivity and specificity of arrhythmia detection methods. However, the sensitivity and specificity of such rate- or interval-based arrhythmia detection methods are limited to the reliability of sense amplifiers in accurately sensing P-waves and/or R-waves and by the selection of the rate zone thresholds for tachycardia detection. Interval-based arrhythmia detection schemes that rely primarily on P-wave and R-wave sensing are subject to limitations due to oversensing and undersensing of depolarization signals, which can result in either overestimating or underestimating the actual heart rate. Inadequately programmed rate zone thresholds can also cause over- or under-detection of tachycardias that might be responsive to ICD therapy.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
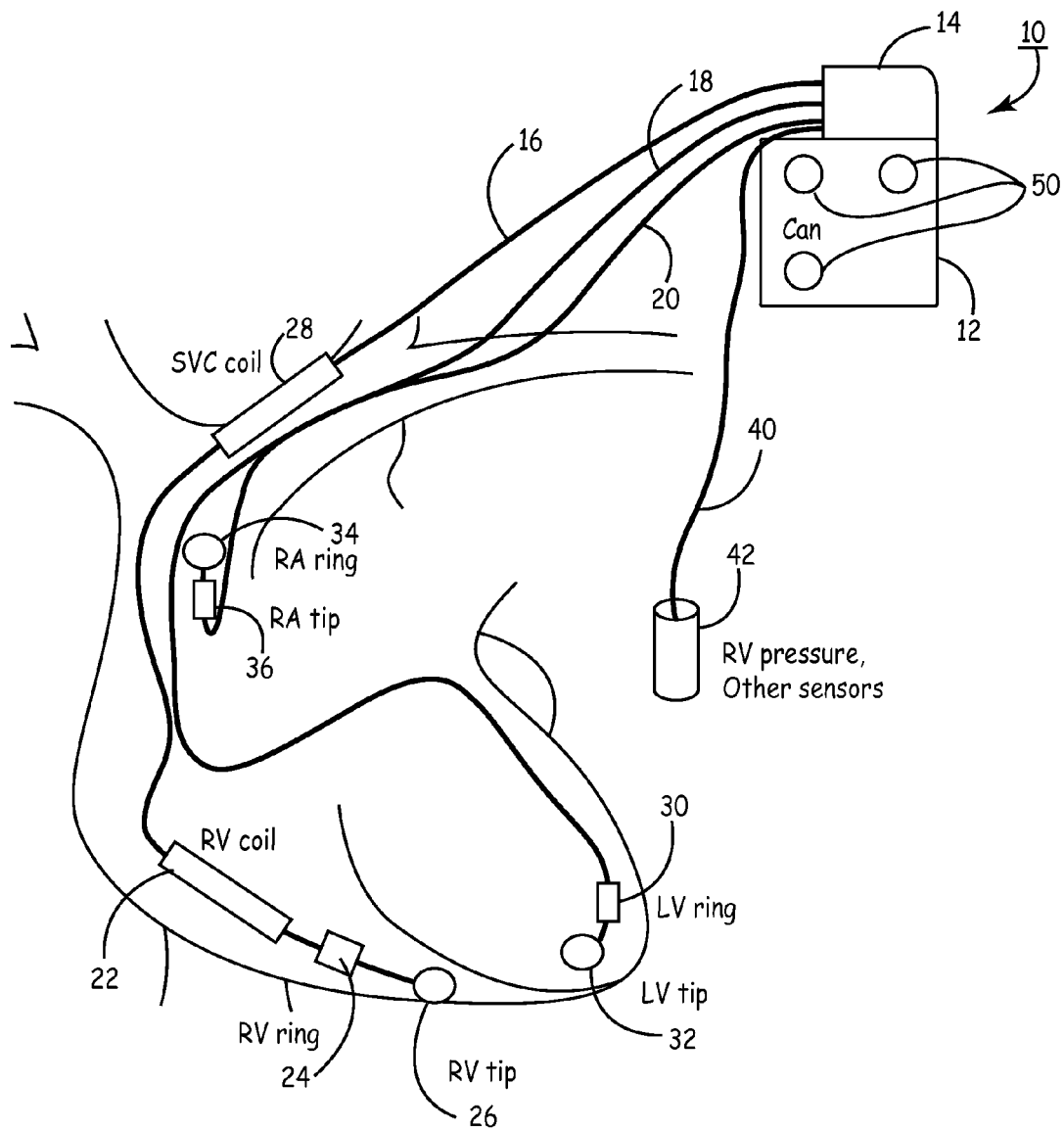
FIG. 1 is an illustration of an implantable cardioverter defibrillator (ICD) in which embodiments of the present invention may be implemented.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. The term "tachycardia" as used herein refers to tachycardia and fibrillation inclusively, and, unless specified, is used to refer generally to both atrial and ventricular tachycardias, including ventricular tachycardia (VT), ventricular fibrillation (VF), atrial fibrillation or flutter (AF) and atrial tachycardia (AT).

FIG. 1 is an illustration of an implantable cardioverter defibrillator (ICD) in which embodiments of the present invention may be implemented. ICD 10 is shown coupled to a patient's heart via leads 16, 18 and 20. Ventricular lead 16 includes a tip electrode 26 and a ring electrode 24. Electrodes 24 and 26 are used for bipolar ventricular pacing and for sensing ventricular EGM signals. While electrodes 24 and 26 may be used for bipolar pacing and sensing, either electrode 24 or 26 may be used in conjunction ICD housing 12, serving as a common or indifferent electrode in a unipolar sensing configuration in some embodiments. Ventricular lead 16 also carries a coil electrode 22 positioned in the right ventricle for delivering high voltage cardioversion/defibrillation (CV/DF) shock pulses. Lead 16 may also carry a superior vena cava (SVC) coil electrode 28, positioned in the superior vena cava, which can be used for electrogram sensing and/or applying CV/DF pulses. Either SVC coil 28 or RV coil 22 may be paired with another electrode for sensing EGM signals.

An atrial lead 20 is used to deploy a tip electrode 36 and a ring electrode 34 in the right atrium of the heart. Electrodes 34 and 36 are used for bipolar atrial pacing and for sensing atrial EGM signals. While electrodes 34 and 36 may be used for bipolar pacing and sensing, either of electrodes 34 and 36 may be used, for example, in conjunction with the surface of ICD housing 12, SVC coil 28 or RV coil 22, for unipolar operation.

A coronary sinus lead 18 is shown operatively positioned relative to the left ventricle. Coronary sinus lead 18 is typically advanced along a cardiac vein via the coronary sinus to position a tip electrode 32 and a ring electrode 30 for pacing and sensing in the left ventricle. It is recognized that coronary sinus lead 18 may additionally carry electrodes for placement along the left atrial chamber for pacing and sensing in the left atrium. Furthermore, while right atrial lead 20 and coronary sinus lead 18 are shown having only tip and ring electrodes, either lead may additionally carry coil electrode for use in high voltage shock delivery.

Each lead 16, 18 and 20 carries electrically-insulated conductors (not shown) for making electrical connection between ICD 10 and the respective electrodes carried by each lead. Leads 16, 18 and 20 are connected to a connector block 14 of ICD 10 thereby electrically coupling the conductors and various electrodes to electronic circuitry hermetically enclosed within housing 12. ICD 10 may also receive far-field EGM signals, also referred to as "subcutaneous ECG signals," from subcutaneous sensing electrodes 50 incorporated on housing 12 or carried by a subcutaneous lead extending from ICD 10. A subcutaneous electrode array for sensing far-field EGM signals is generally disclosed in U.S. Pat. No. 6,522,915 (Ceballos, et al.),hereby incorporated herein by reference in its entirety.

ICD 10 may additionally be coupled to one or more physiological sensors 42. As used herein, "physiological sensor" refers to any type of sensor generating a signal responsive to physiological events or conditions. Such sensors include, for example, pressure sensors, flow sensors, accelerometers or other motion sensors, acoustical sensors, temperature sensors, and blood or tissue chemistry sensors such as oxygen saturation and pH sensors. Physiological sensor 42 is shown carried by a separate lead 40 coupled to ICD 10. In various embodiments, sensor 42 may be positioned in any subcutaneous, submuscular, epicardial, transvenous, or intracardiac location. As such, one or more physiological sensors may alternatively be carried by any of the transvenous leads 26, 18 and 20 or incorporated in or on ICD housing 12.

The embodiment shown in FIG. 1 is illustrative in nature and is not intended to be limiting with regard to the particular type of device in which embodiments of the present invention may be practiced. It is recognized that various implantable medical device systems employing methods described herein may be associated with a variety of single chamber, dual chamber and multi-chamber devices and associated lead and electrode configurations, including devices with leads in the RV only, leads in the RA and RV, and leads in the RA, RV, coronary vein (LV). Methods described herein may be implemented in any medical device system that includes electrodes for sensing one or more near-field or far-field EGM signals. Furthermore, such systems are not limited to ICD systems but include, for example, implantable or external monitoring systems that do not necessarily include pacing or CV/DF shock delivery capabilities.

Figure 2:
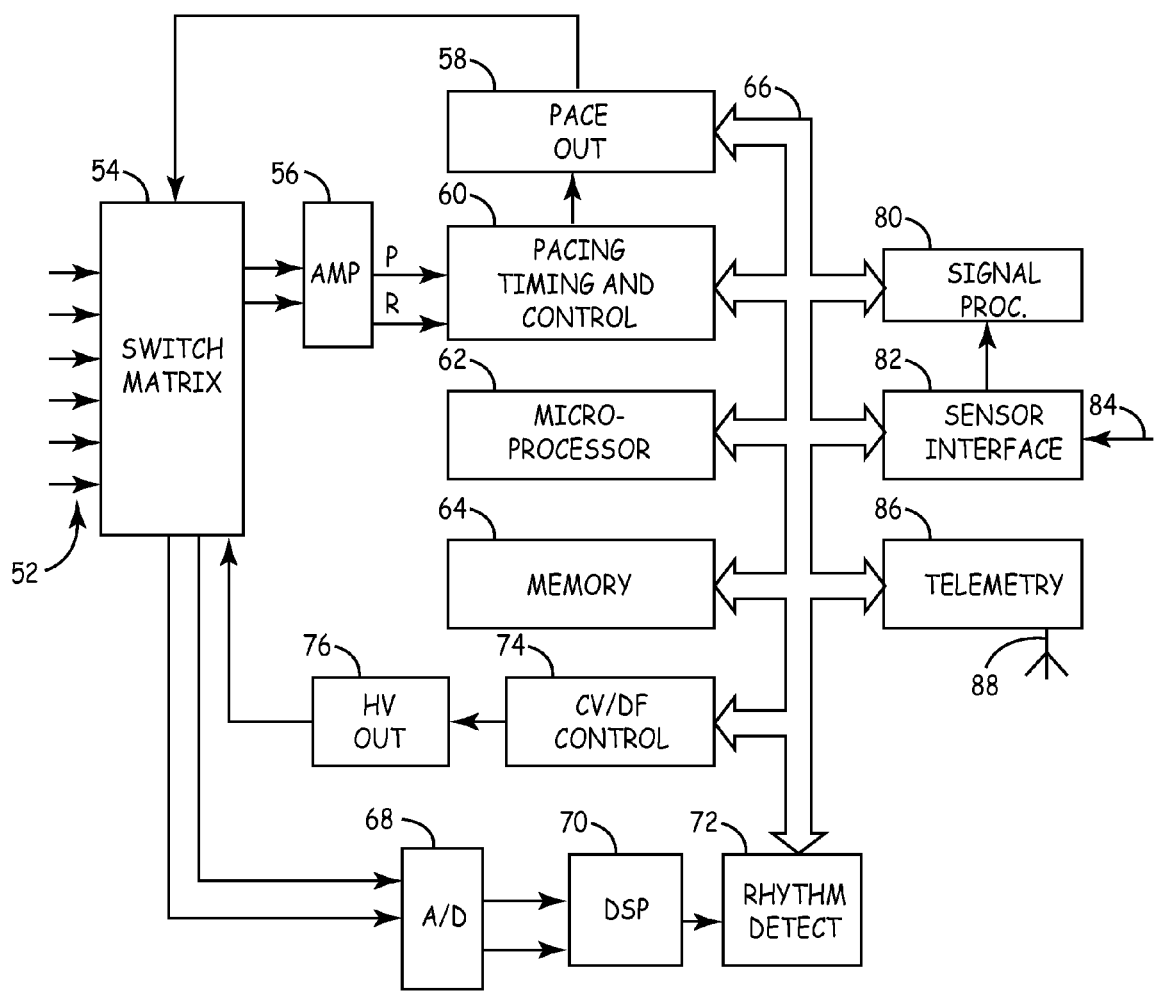
FIG. 2 is a functional block diagram of an implantable ICD according to one embodiment of the invention.

FIG. 2 is a functional block diagram of an implantable ICD according to one embodiment of the invention. ICD 10 generally includes pacing timing and control circuitry 60, cardioversion/defibrillation (CV/DF) control circuitry 74 and an operating system that may employ microprocessor 62 or a digital state machine for timing sensing and therapy delivery functions and controlling other device functions in accordance with a programmed operating mode. Microprocessor 62 and associated memory 64 are coupled to the various components of ICD 10 via a data/address bus 66. ICD 10 includes pacing output circuitry 58 for generating cardiac pacing pulses, under the control of pacing timing and control 60. High voltage output circuitry 76 delivers high-voltage CV/DF shocking pulses under the control of CV/DF control 74. Pacing output 58 and HV output 76 may correspond, for example, to circuitry generally disclosed in U.S. Pat. No. 6,731,978 to Olson et al., hereby incorporated herein by reference in its entirety.

As used herein, monitoring a "heart rate" refers to the determination of depolarization intervals using sensed depolarization signals. ICD 10 monitors the heart rate by sensing depolarization signals using any of the available electrodes 52 coupled to sense amplifier 56 via switch matrix 54. "Heart rate" monitoring is used for determining a need for bradycardia pacing or controlling the timing of pacing pulses relative to intrinsic cardiac events.

As used herein, monitoring a "heart rhythm" refers to the detection and discrimination of sinus and non-sinus heart rhythms and malignant and non-malignant heart rhythms using EGM morphology analysis. As will be described herein, heart rhythm monitoring does not depend on heart rate monitoring. In other words, heart rhythm monitoring does not require sensing depolarization signals or determining depolarization intervals as a first step. ICD 10 monitors the heart rhythm using any of the available electrodes 52 coupled to analog-to-digital converter 68 via switch matrix 54. ICD 10 monitors the heart rhythm for determining a need for high voltage CV/DF therapy, anti-tachycardia pacing therapies, or other therapies for treating non-sinus tachycardias, particularly malignant forms of tachycardia, and/or for storing arrhythmia episode data for use in diagnostic purposes.

Electrodes used for sensing and electrodes used for delivering electrical stimulation therapies in response to both heart rate monitoring and heart rhythm monitoring are selected via switch matrix 54. When used for sensing a heart rate, electrodes 52 are coupled to sense amplifier(s) 56, which typically take the form of an automatic gain controlled amplifier providing an adjustable sensing threshold as a function of the measured P-wave or R-wave amplitude. The required number of sense amplifiers is provided for sensing multiple EGM signals. For example, both atrial and ventricular signals may be received by separate an atrial sense amplifier and ventricular sense amplifier for sensing both P-waves for determining an atrial rate and R-waves for determining a ventricular rate, respectively. P and R output signals are generated by sense amplifier(s) 56 whenever an atrial or ventricular sensed signal, respectively, exceeds the present sensing threshold. The general operation of amplifier(s) 56 may correspond to that disclosed in U.S. Pat. No. 5,117,824, by Keimel et al, incorporated herein by reference in its entirety or may be accomplished by a less sensitive approach such as a fixed threshold sense amplifier approach used by standard bradycardia pacemakers.

Pacing timing and control typically includes escape interval timers which are reset upon sensing of R-waves and P-waves. Upon expiration of an escape interval timer, a pacing pulse is generated by pacing output 58 coupled to the appropriate electrodes 52 via switch matrix 54. The escape interval timers are reset upon pacing pulse delivery and thereby control the basic timing of cardiac pacing functions. The durations of the escape intervals are determined by microprocessor 62, in response to stored data in memory 64 and are communicated to the pacing timing and control 60 via address/data bus 66. Pacing timing and control 60 also determines the amplitudes and pulse widths of scheduled cardiac pacing pulses under control of microprocessor 62.

In past practice, the value of the count present in the escape interval timers when reset by sensed R-waves and P-waves has been used to measure the durations of R-R intervals, P-P intervals, P-R intervals, and R-P intervals. These intervals, generally referred to herein as "depolarization intervals," between sensed cardiac events (P-waves and R-waves) have been used in past practice to detect arrhythmia episodes in rate- or interval-based detection algorithms, for example using predefined interval zones as described previously in the "Background". Once a tachycardia or fibrillation episode is detected based on depolarization interval measurements, the morphology of the EGM signal may be used in discriminating between different types of tachycardia. As such, in past practice, arrhythmia detection generally begins by detecting a fast heart rate using measured depolarization intervals. Once a preliminary arrhythmia detection is made based on depolarization intervals, interval patterns and morphology information can be used for classifying the heart rhythm.

In contrast to such interval-based algorithms, methods for detecting heart rhythm described herein are based on morphology analysis of EGM signal segments, without requiring sensing of cardiac depolarizations or measurement of depolarization intervals. When used for detecting a heart rhythm, selected electrodes 52 are coupled to A/D converter 68 via switch matrix 54. Digital signal processor 70 receives the digitized EGM signal and provides morphology parameter values to rhythm detection module 72. As will be described in detail herein, rhythm detection module includes logic circuitry operating to detect a heart rhythm based on the morphology parameter values derived from one or more sensed EGM signals acquired over a predefined signal processing time window.

Upon detecting a heart rhythm, signals generated by rhythm detection module 72 are provided to CV/DF control 74 for controlling high voltage output 76 to deliver CV/DF therapies as needed to treat a detected tachycardia. Heart rhythm detection signals are also provided to pacing timing and control 60 via bus 66 for controlling the delivery of anti-tachycardia pacing therapies when appropriate. As such, P and R output signals generated by sense amplifier 56 are used by pacing timing and control for controlling pacing functions during bradycardia pacing and for timing or synchronizing pacing pulses to intrinsic events during the delivery of other pacing therapies such as cardiac resynchronization therapy or anti-tachycardia pacing. P and R output signals, however, are not necessarily received by rhythm detection module 72 for use in detecting the heart rhythm. While P and R output signal generated by sense amplifier 56 can be used in some embodiments as secondary signals for confirming or classifying a heart rhythm detection made in response to EGM morphology analysis, it is EGM morphology analysis, not sensed depolarization signals, that provides the primary rhythm detection parameters used by heart rhythm detection module 72.

ICD 10 may further include one or more physiological sensors 84 for sensing physiological signals other than cardiac electrical signals. Physiological sensor 84 may be embodied as any of the physiological sensors mentioned previously or other physiological sensor known for use with implantable medical devices. Sensor 84 is coupled to ICD 10 via a sensor interface 82 which provides sensor signals to signal processing circuitry 80. Sensor signals are used by microprocessor 62 for detecting physiological events or conditions. For example, IMD 10 may monitor heart wall motion, blood pressure, blood chemistry, respiration, or patient activity. One or more sensor signals may also be used by rhythm detection module 72 in confirming or classifying a heart rhythm detected according to an EGM morphology-based detection algorithm.

The operating system includes associated memory 62 for storing a variety of programmed-in operating mode and parameter values that are used by microprocessor 62. The memory 64 may also be used for storing data compiled from sensed signals and/or relating to device operating history for telemetry out on receipt of a retrieval or interrogation instruction.

ICD 10 further includes telemetry circuitry 86 and antenna 88. Programming commands or data are transmitted during uplink or downlink telemetry between ICD telemetry circuitry 86 and external telemetry circuitry included in a programmer or home monitoring unit.

Figure 3:
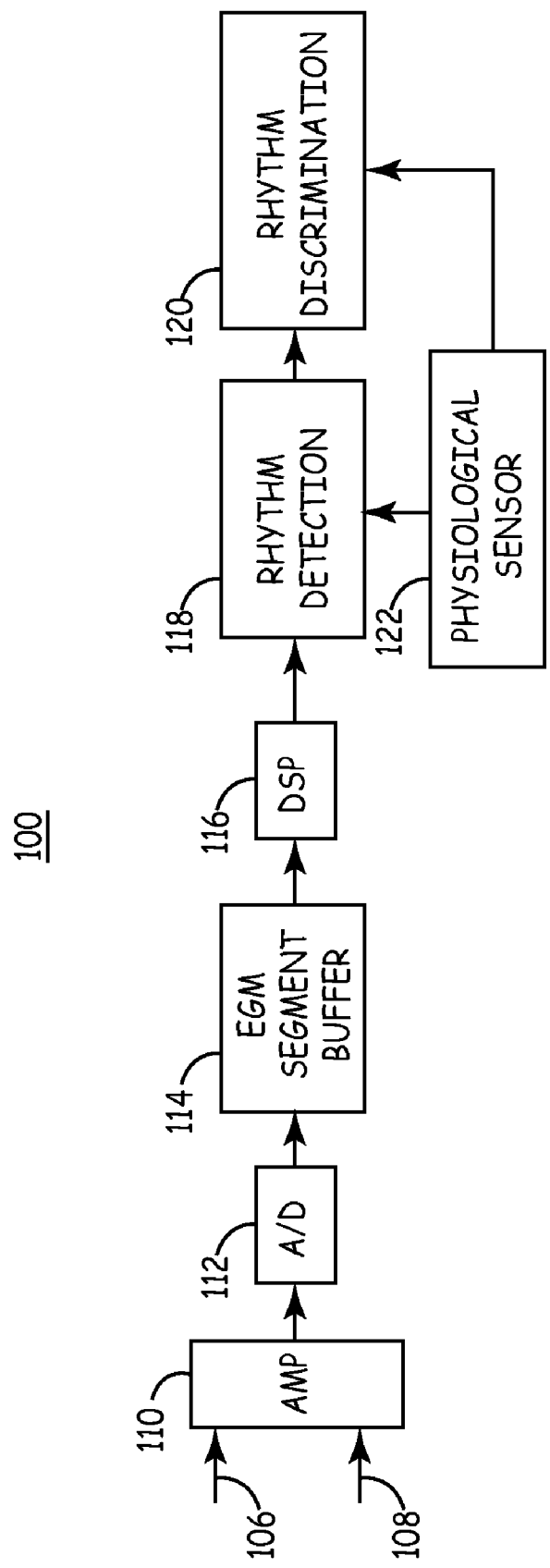
FIG. 3 is a functional block diagram of heart rhythm detection circuitry according to one embodiment of the invention.

FIG. 3 is a functional block diagram of heart rhythm detection circuitry according to one embodiment of the invention. One or more EGM signals 106 and 108 are received by amplifier 110 and passed to analog-to-digital converter 112. In one embodiment, one near-field EGM signal and one far-field EGM signal are received by amplifier 110. In alternative embodiments, two near-field or two far-field EGM signals may be received. The sampled and filtered EGM signal stream is provided to digital signal processor (DSP) 116 in segments by buffer 114. The digitized EGM signals are processed by DSP 116 over a signal processing window or segment having a predefined time duration or number of signal samples. In past practice, morphology analysis performed secondary to interval-based tachycardia detection has typically been performed on a cycle-by-cycle basis. For example, the EGM signal over one cardiac cycle, or parameters derived therefrom, might be compared to a signal template corresponding to one cardiac cycle during a known heart rhythm. As such, the secondary morphology analysis performed according to past practices is typically performed over intervals that begin and end relative to one or more cardiac cycles. In other words, the morphology processing windows are typically defined by sensing depolarization signals. The processing window applied to an EGM signal by DSP 116 is defined in time without sensing cardiac depolarizations such that the beginning and end of the processing window are independent of the temporal location of depolarization signals.

It is recognized that the EGM signals may be filtered prior to processing by DSP 116 to reduce or eliminate noise. Filtering should only be used as necessary, however, and filtering frequencies should be carefully selected since EGM morphology changes due to filtering are undesirable. Significant alterations of the EGM signal morphology due to filtering may reduce the effectiveness of morphology-based heart rhythm detection algorithms. Additional filtering of the EGM signal during the DSP processing may be performed depending on the specific algorithms needed for the heart rhythm detection algorithms.

In one embodiment, three-second signal processing windows, also referred to herein as "segments", are processed by DSP 116, although longer or shorter segments may be processed. The signal segment length is selected to provide a snapshot of the current heart rhythm such that distinct morphology characteristics associated with various arrhythmia types can be identified from the segment thereby allowing the rhythm to be correctly classified.

Tachycardia detection module 118 detects tachycardia episodes, which may include VT, VF, AT, AF, etc., based on results provided by DSP 116. Tachycardia discrimination module 120 may perform additional algorithms for discriminating between tachycardia types by evaluating other morphological characteristics of one or both EGM input signals 106 and 108 and/or input from a physiological sensor module 122 and optionally depolarization intervals provided by a sense amplifier when present. It is recognized that tachycardia detection module 118 may also receive input from physiological sensor module 122 for use in making the initial tachycardia detection.

Physiological sensor module 122 provides any physiological signal information sensed by an implantable physiological sensor, which is not derived from an EGM signal. Physiological sensor 122 typically provides metabolic or hemodynamic signal information, which is often derived from mechanical or chemical signals but can also be derived from electrical signals, e.g. electrical impedance signals measured for monitoring respiration or changes in cardiac volume. Physiological sensor module 122 may provide information relating to, for example, a blood pressure signal such as a right atrial pressure or right ventricular pressure, a blood chemistry signal such as an oxygen saturation signal or pH signal, a temperature signal, an accelerometer signal, or a subcutaneous photoplethysmography signal. Physiological sensor module 122 may include a separate amplifier, filters or other signal conditioning circuitry and may include a separate DSP or utilize DSP 116.

Figure 4:
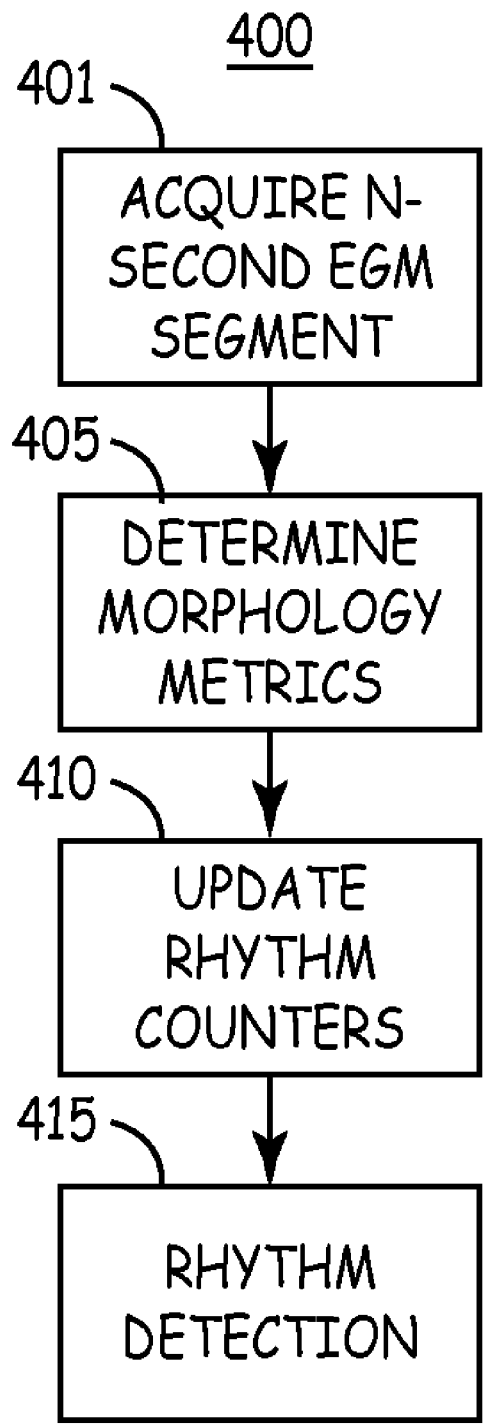
FIG. 4 is a flow chart of a morphology-based heart rhythm detection method according to one embodiment of the invention.

FIG. 4 is a flow chart of a morphology-based heart rhythm detection method according to one embodiment of the invention. Flow chart 400 and other flow charts presented herein are intended to illustrate the functional operation of a medical device performing the method, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 401, an EGM signal is digitized and segmented into N-second processing windows. EGM signals may be acquired from one or more EGM sensing vectors, e.g. at least one near-field sensing vector and one far-field sensing vector. The sampling rate of the EGM signal may be on the order of 125 Hz to 1000 Hz. Morphology-based rhythm detection methods described herein are expected to have high sensitivity for tachycardia detection over this entire range of sampling rates. Higher sampling rates, e.g. 250 Hz or greater, may provide greater specificity in correctly classifying tachycardia episode types depending on the detection and classification parameters implemented. Typical sampling rates used in currently available implantable medical devices are on the order of 128 to 256 Hz.

At block 405, a digitized EGM segment is processed for determining a number of morphology metrics. It is recognized that morphology metrics may be determined from multiple EGM sensing signal segments that are acquired from different sensing vectors, either simultaneously over the same n-second processing window or during n-second processing windows that sequential or temporally offset.

A number of rhythm counters are updated at block 410 in response to the determined morphology metrics, as will be described in greater detail below. A rhythm counter is defined for each of the rhythm types to be detected, including, for example, sinus rhythm, VT, VF, supraventricular tachycardia (SVT), AT, and AF. After updating each rhythm counter, the counter values are used to detect the heart rhythm at block 415. Rhythm detection is performed by a microprocessor or logic circuitry using the rhythm counter values as inputs as well as any of the determined morphology metric values and other physiological sensor information.

Figure 5:
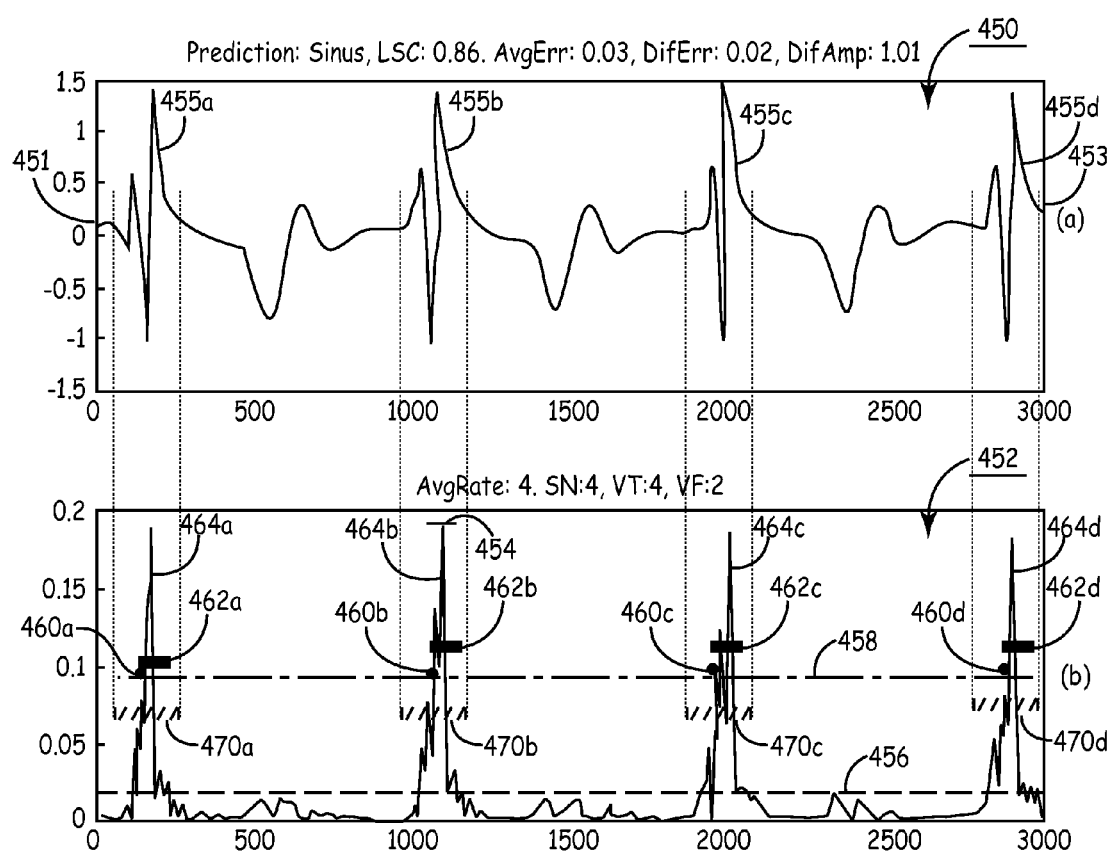
FIG. 5 is a sample recording of an EGM signal segment and the first derivative of the EGM signal.

FIG. 5 is a sample recording of an EGM signal segment and the first derivative of the EGM signal. The EGM signal segment 450 is a three-second segment obtained during normal sinus rhythm. As can be seen in FIG. 5, the beginning 451 of the signal segment 450 and the end 453 of segment 450 are not timed relative to the R-wave depolarization signals 455*a* through 455*d*. Segment 450 does not start or end at any particular point in a cardiac cycle but is merely a time window, which can be applied randomly relative to the depolarization signals 455*a* through 455*d*.

The first derivative 452 of the EGM signal segment is shown in the lower panel. The first derivative 452 of the EGM signal is referred to hereafter as the "slope signal" because it is used to estimate the slope content of the EGM signal. The slope signal 452 is the rectified difference between successive sample points (or non-successive paired sample points) of EGM signal segment 450. In one embodiment, the slope signal will be used to compute all morphology metrics for each EGM signal segment.

In one embodiment, the morphology metrics include a low slope content (LSC), a cardiac cycle number (CCN) and template variability metrics. The LSC is approximated as the ratio of the number of slope signal points having an absolute value below a low slope threshold 456 to the total number of slope signal points determined from the slope signal 452 during the n-second segment. The low slope threshold 456 is based on the slope content of the slope signal 452. For example, the low slope threshold 456 may be defined as percentage, for example 10%, of the largest absolute slope 454 determined from the slope signal 452. The LSC is then determined as the number of slope signal data points having an absolute value less than the low slope threshold 456 to the total number of slope signal data points occurring in the signal segment.

The LSC of non-shockable tachycardias is typically low relative to the LSC of shockable tachycardias. As such, the LSC is a useful morphology parameter to monitor for discriminating between non-sinus and sinus tachycardias and determining when tachycardia therapies are needed. As used herein, the term "shockable rhythm" refers to malignant or life threatening ventricular tachyarrhythmias, which can be terminated by cardioversion/defibrillation (CV/DF) shock delivery. "Non-shockable" refers to non-malignant heart rhythms, such as sinus tachycardia, that are not life threatening.

The cardiac cycle count is determined as an indication of the average heart rate during the n-second segment. As can be seen in FIG. 5, the slope signal 452 will include sharp spikes 464*a* through 464*d* corresponding to each depolarization (R-wave) on the EGM signal 450. As such, a cardiac cycle count can be determined as the number of slope signal spikes 464*a* through 464*d* occurring over the n-second segment. The number of slope signal spikes 464*a* through 464*d* occurring during the n-second segment are determined by counting the first slope signal time points 460*a* through 460*d* that exceed a cardiac cycle threshold 458. Each counted point 460*a* through 460*d* is followed by a blanking window 462*a* through 462*d* during which no points will be counted to prevent double-counting the same cardiac cycle. The cardiac cycle threshold 458 may be defined as a percentage, for example 25% to 75% of the maximum slope signal value 454.

The template variability metrics refer to one or more morphology metrics derived from the comparison of each EGM signal spike (R-wave) 455*a* through 455*d* to a template, for example an averaged EGM signal spike template determined by averaging all EGM signal spikes occurring during the n-second segment. Non-shockable rhythms typically present a monomorphic depolarization signal, i.e. the R-waves or P-waves possess a regular morphology from beat to beat. Shockable rhythms typically present a polymorphic depolarization signal in that the signal is more chaotic or inconsistent from beat-to-beat. As such, a comparative analysis of the morphology of the EGM signal spikes 455a through 455d is made to provide additional metrics relating to the variability of the EGM signal morphology for use in detecting heart rhythms.

A morphology window 470a through 470d is defined relative to each time point 460a through 460d that exceeds the cardiac cycle threshold 458. The morphology window may be on the order of 150 to 200 ms and may be centered or shifted relative to the time points 460a through 460d. In one embodiment, the morphology window 470a begins 50 ms prior to the time point 460a and ends 130 ms after the time point 460a. The EGM signal points within each morphology window 470a through 470d are then aligned and averaged point by point to obtain an average EGM signal template. The individual EGM signals within each morphology window 470a through 470d are then compared to the average EGM signal template to obtain one or more "template variability metrics." As such, the template variability metrics relate to the variability of the EGM signal from one cardiac cycle to the next and are thus an indication of polymorphic or monomorphic rhythms.

Figure 6:
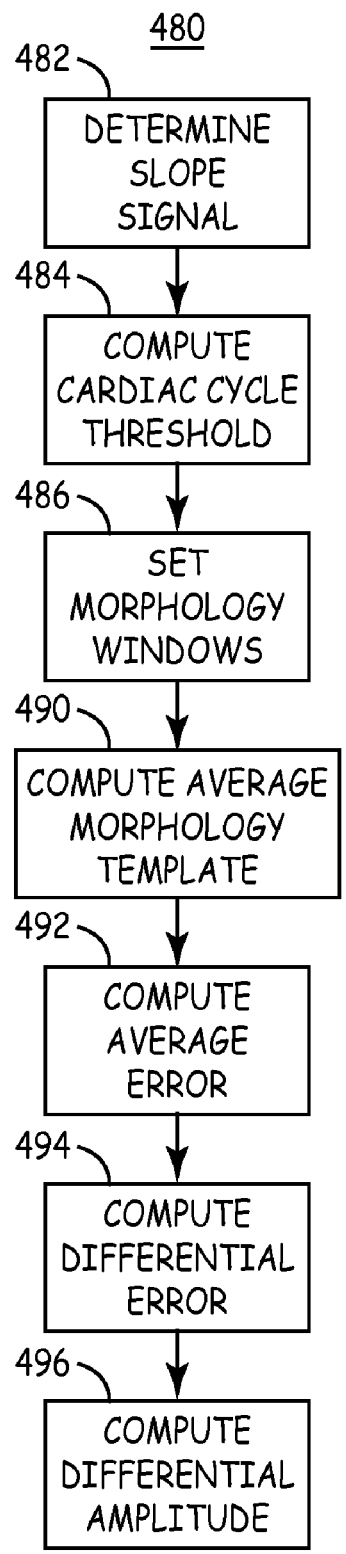
FIG. 6 is a flow chart summarizing one method for computing template variability metrics.

FIG. 6 is a flow chart summarizing one method for computing template variability metrics. At block 482, the slope signal is determined as the first derivative of the EGM signal acquired over the n-second segment as described above. At block 484, the cardiac cycle threshold is computed based on a maximum slope signal absolute value. The morphology windows are set at block 486 relative to the first time point of each slope signal spike exceeding the cardiac cycle threshold. The average morphology template is then computed by averaging the EGM signal within each morphology window point-by-point at block 490.

At block 492, an average error is computed. The average error is computed by first determining the error between the EGM signal during each morphology window and the averaged template. The individual EGM signals for each morphology window are referred to hereafter as the "aligned EGM signals" since they are each "temporally aligned" with the averaged template to determine the template variability metrics.

The error (Err) between each aligned EGM signal and the averaged template is computed as:

$$\text{Err}_i = \{\text{SUM}_{j=1,M} |\text{AlignedSS}_{ij} - \text{Template}_j|\} / \{\text{SUM}_{j=1,M} |\text{Template}_j|\}$$

wherein M is the number of EGM signal sample points occurring in each morphology window, i.e. the number of points in each aligned signal EGM (AlignedSS$_i$) and in the averaged template (Template).

The average error (AVG ERR) is then computed as:

$$\text{AVG ERR} = (1/N) * \{\text{SUM}_{i=1,N}(\text{Err}_i)\}$$

wherein N is the number of aligned EGM signals occurring in the n-second segment.

The differential error (DIFF ERR) is computed at block 494 as the difference between the maximum error and the minimum error computed for the N aligned EGM signals:

$$\text{DIFF ERR} = \text{MAX}(\text{Err}_i) - \text{MIN}(\text{Err}_i)$$

The differential amplitude is computed at block 496 by first determining the maximum EGM signal amplitude (MaxAmp) occurring during each of the aligned EGM signals. The differential amplitude (DIFF AMP) is then computed as the ratio of the maximum or largest of the maximum EGM signal amplitudes (MAX(MaxAmp)) to the minimum or lowest of the maximum EGM signal amplitudes (MIN(MaxAmp)):

$$\text{DIFF AMP} = \text{MAX (MaxAmp)} / \text{MIN(MaxAmp)}$$

Relatively low values of averaged error, differential error and differential amplitude are generally indicative of a non-shockable, monomorphic rhythm whereas higher values indicate shockable, polymorphic rhythms.

Figure 7:
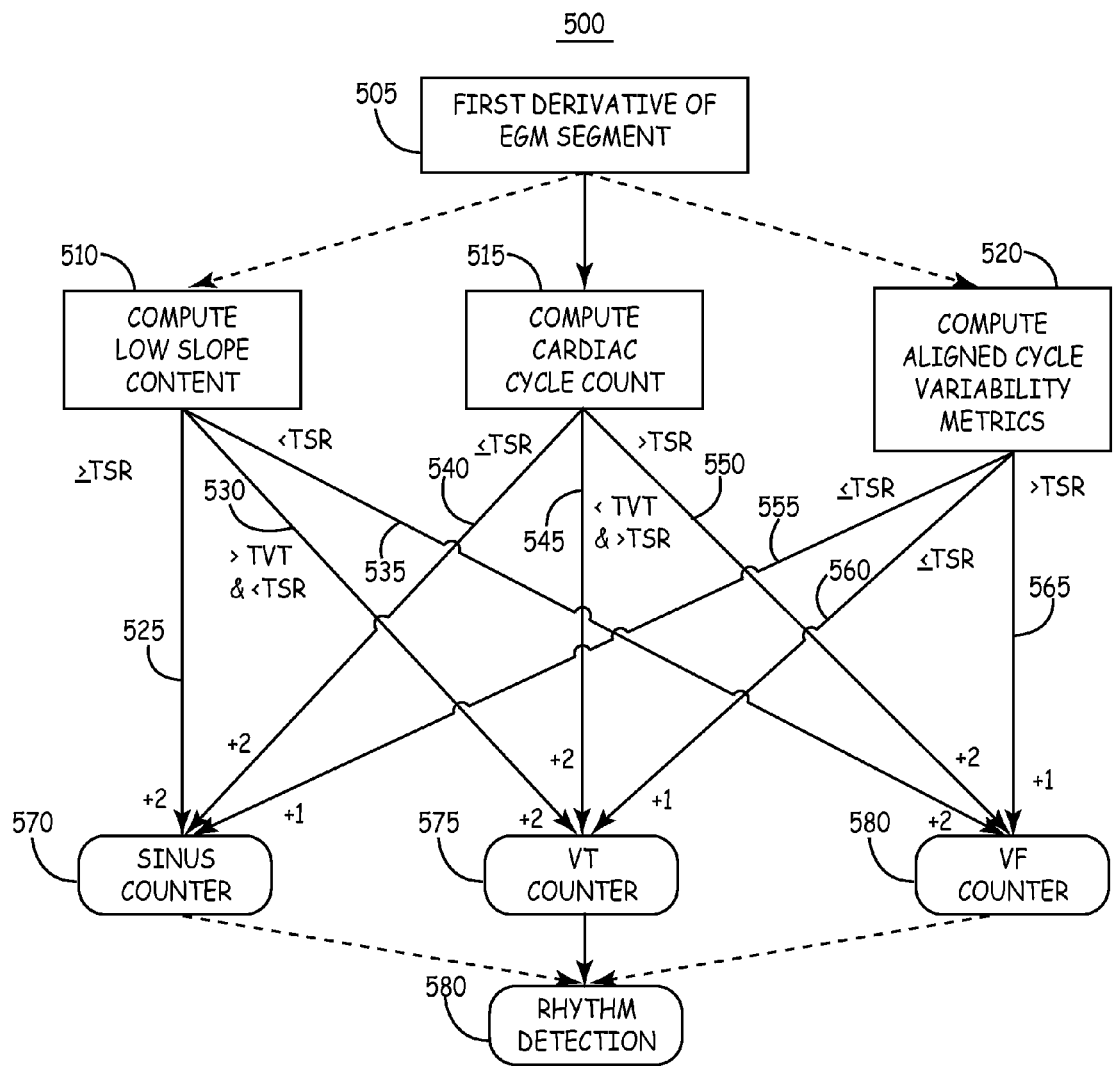
FIG. 7 is a flow chart of one morphology-based heart rhythm detection method.

FIG. 7 is a flow chart of one morphology-based heart rhythm detection method 500. The method 500 relates to the detection of ventricular rhythms but it is understood that method 500 could be adapted for the detection of atrial rhythms. At block 505, the first derivative of the sampled EGM signal(s) is computed as the differences between consecutive sampled points to obtain the slope signal. The slope signal sample points are used in computing a number of morphology metrics corresponding to an EGM signal processing window having a predefined duration, e.g. three seconds. At block 510, a LSC metric is computed, for example as described in conjunction with FIG. 5. At block 515 a cardiac cycle count is derived from the slope signal by counting the number of slope signal spikes as described in conjunction with FIG. 5. At block 520, a number of metrics relating to the variability of the aligned EGM signal cycles are computed, e.g. the averaged error, differential error and differential amplitude as described in conjunction with FIG. 6.

Each of the morphology metrics computed at block 510, 515 and 520 are compared to respective threshold values defined for detecting and discriminating sinus and non-sinus rhythms. A number of rhythm counters 570, 575 and 580 are defined according to each of the rhythm types to be detected. The rhythm counters are increased in response to particular threshold criterion being met for a given metric.

The LSC computed at block 510 is compared to a sinus rhythm threshold value (TSR) defined for discriminating sinus rhythms from shockable VT or VF. A high LSC is indicative of non-shockable, sinus rhythms. If the LSC is greater than or equal to the sinus rhythm threshold, as indicated by path 525, a sinus rhythm counter 570 is updated. Each morphology metric is associated with a weighting factor indicating the increment by which a particular a rhythm counter is increased when an associated rhythm threshold criterion is met. LSC is shown having a weighting factor of +2 in FIG. 7 such that sinus rhythm counter 570 is increased by two when the LSC is greater than or equal to the sinus rhythm threshold (TSR).

If the LSC is less than the sinus rhythm threshold but greater than a VT threshold, the VT rhythm counter 575 is increased by two as indicated by path 530. If the LSC is less than the sinus rhythm threshold, the VF rhythm counter 580 is increased by two as indicated by path 535. As such, both the VT and VF counters 575 and 580 will be increased when the LSC falls between the sinus rhythm threshold and the VT threshold.

If the cardiac cycle count falls below a sinus rhythm threshold defined for the cardiac cycle count, as indicated by path 540, the sinus rhythm counter is increased by two. If the cardiac cycle count falls between a VT threshold and the sinus rhythm threshold defined for the cardiac cycle count, the VT rhythm counter 575 is increased by two as indicated by path 545. If the cardiac cycle count is greater than the sinus rhythm threshold defined for the cardiac cycle count, the VF rhythm counter 580 is increased by two as indicated by path 550. As such, both the VT and the VF rhythm counters are increased by two when the cardiac cycle count falls between the sinus threshold and the VT threshold.

In a similar manner, the aligned cycle variability metrics computed at block 520 are each compared to corresponding thresholds defined for each metric. In one embodiment, each of the averaged error, differential error and differential amplitude, computed as described in conjunction with FIG. 6, are compared to a respective sinus rhythm threshold, referred to generically in FIG. 7 as TSR but defined separately for each of the averaged error, differential error and differential amplitude metrics. Both the sinus rhythm counter 570 and the VT rhythm counter 575 are increased by one for each of the aligned cycle variability metrics falling below a corresponding sinus rhythm threshold, as indicated by paths 555 and 560. The VF rhythm counter 580 is increased by one for each of the aligned cycle variability metrics that is greater than a corresponding sinus rhythm threshold, as indicated by path 565.

Once all rhythm counters 570, 575, and 580 have been updated according to the morphology metrics computed for the current EGM signal segment, a rhythm detection is made at block 580. While weighting factors of two and one are used in the example shown in FIG. 7, it is recognized that other weighting factors may be used, including negative weighting factors, depending on the particular metric and its relationship to a particular rhythm. The rhythm detection is made at block 580 in response to the rhythm counter values and can thus be made based only on morphology metrics derived from an EGM signal segment without requiring sensing of depolarization signals or measuring depolarization intervals. A rhythm detection is made at the end of each time segment, or every three seconds in the given example. It is recognized that in alternative embodiments, staggered time segments may be processed using the same or different EGM sensing vector signals such that rhythm detection may be made more frequently, i.e. at the end of each staggered time segment.

It is further recognized that multiple EGM signals may be processed according to the method shown in FIG. 7, in either a simultaneous, staggered or sequential manner. One set of rhythm counters can be updated in response to the metrics computed from all of the multiple EGM sensing vectors. Alternatively, separate sets of rhythm counters may be provided for each EGM sensing vector. In the latter case, one set of rhythm counters updated according to morphology metrics computed from one sensing vector signal may be used to confirm a rhythm detection made based on another set of rhythm counters. In the former case, morphology metrics computed from different sensing vectors may be weighted differently for incrementing the common set of rhythm counters. For example, a rhythm counter may be updated by different increments in response to the same morphology metric depending on which sensing vector signal was used to derive the metric. In one embodiment, a morphology metric derived from a near-field signal may be assigned a greater increment than the same morphology metric derived from a far-field signal and vice versa.

As shown previously in FIG. 3, other physiological sensor signals may be used for rhythm detection at block 580. Such physiological sensor signals may be analyzed over the n-second processing window for deriving morphology metrics in a manner analogous to the EGM signal processing shown in FIG. 7. Alternatively, physiological event detection or measurement of physiological conditions such as changes in blood pressure, changes in blood oxygen saturation, changes in myocardial wall motion, etc. may be used to detect or confirm a heart rhythm at block 580.

Figure 8:
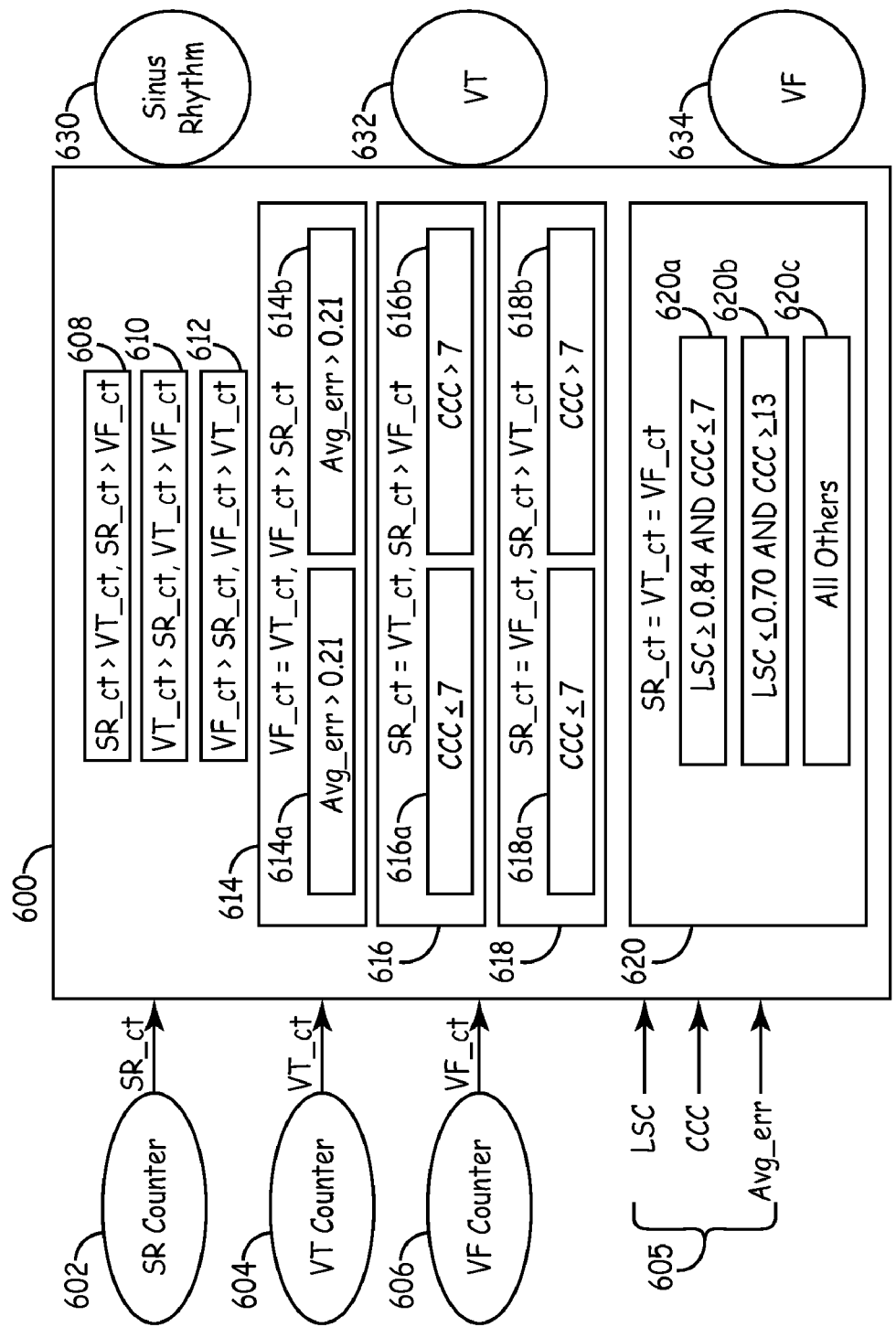
FIG. 8 is a block diagram of a logic circuit used for detecting a heart rhythm using inputs from rhythm counters described in conjunction with FIG. 7.

FIG. 8 is a block diagram of a logic circuit used for detecting a heart rhythm using inputs from the rhythm counters described in conjunction with FIG. 7. Logic circuit 600 receives each of the rhythm counter values as inputs 602, 604 and 606. If any one of the rhythm counter input values 602, 604, and 606 is greater than all of the other rhythm counter input values, as determined by the comparative blocks 608, 610 and 612, then the output signal 630, 632 or 634 from logic circuit 600 corresponds to the rhythm counter having the greatest count. For example, if the sinus rhythm (SR) counter value 602 is greater than both of the VT rhythm counter input value 604 and the VF rhythm counter input value 606, as determined by comparative block 608, logic circuit 600 provides an output signal 630 corresponding to a sinus rhythm detection.

If any two of the rhythm counter inputs 602, 604, and 606 are equal to each other and both are greater than the other rhythm counter(s), additional criteria are applied at logic circuit blocks 614, 616, or 618 to determine the detected rhythm. As such, additional inputs 605 are received by logic circuit 600 for discriminating between heart rhythms when two rhythm counters are equal. In FIG. 8, the additional inputs 605 include the LSC, the cardiac cycle count, and the averaged error of the aligned cardiac cycles. It is recognized that other morphology metrics and/or other physiological sensor signal information could be provided as inputs to logic circuit 600.

At block 614, the averaged error is compared to a VF threshold value when the VF and VT rhythm counters are equal to each other and both greater than the sinus rhythm counter. If the averaged error is greater than the VF threshold value, as indicated at block 614a, the output signal of logic circuit 600 corresponds to a VF detection 634. If the averaged error is less than or equal to the VF threshold value, as indicated at block 614b, logic circuit 600 generates a VT detection output signal 632.

At block 616, the cardiac cycle count is compared to a sinus rhythm threshold when the sinus rhythm counter and the VT rhythm counter are equal to each other and both are greater than the VF rhythm counter. If the cardiac cycle count is less than or equal to the sinus rhythm threshold, as indicated at block 616a, a sinus rhythm output signal 630 is generated. If the cardiac cycle count is greater than the sinus rhythm threshold, a VT detection output signal 632 is generated.

Similar operations are performed at block 618, when the sinus rhythm counter and the VF rhythm counter are equal to each other and both are greater than the VT rhythm counter. If the cardiac cycle count (CCC) is less than or equal a sinus rhythm threshold, a sinus rhythm detection is made (630). If the cardiac cycle count is greater than the sinus rhythm threshold, a VF detection is made (634).

The VF threshold for averaged error is shown to be 0.21 and the sinus rhythm threshold for cardiac cycle count is shown to be seven in FIG. 8. It is recognized that the threshold values used by logic circuit 600 may be defined differently in other embodiments and will depend on the methods used for deriving the morphology metrics and the length of the EGM signal processing window. The thresholds may be programmable values that can be tailored to physician preference or a particular patient.

The situation of all rhythm counters being equal is handled by logic circuit block 620. Logic operations performed at block 620 involve comparisons of both the LSC and the cardiac cycle count to various thresholds. If the LSC is greater than or equal to a sinus rhythm threshold and the cardiac cycle count is less than or equal to the sinus rhythm threshold, as determined at block 620, a sinus rhythm detection is made (630). If the LSC is less than or equal to a VF threshold and the cardiac cycle count is greater than or equal to a VF threshold, a VF detection is made (634). Any other conditions (620*c*) result in a VT detection (632). The particular threshold values used may vary between embodiments and are not limited to the values shown in the example of FIG. 8.

The logic circuitry shown in FIG. 8 is intended to be illustrative of the kind of logic operations that may be performed using morphology metrics for detecting a heart rhythm. It is recognized that numerous variations may be conceived by one having skill in the art, which will depend in part on the particular morphology metrics used, the methods for computing the metrics, and the types of heart rhythms to be detected. While the methods described herein refer primarily to detection of ventricular rhythms, it will be appreciated by one having skill in the art that the methods described can be modified to perform atrial rhythm detection additionally or alternatively to ventricular rhythm detection. Furthermore, methods described herein may be adapted for use in any single, dual or multi-chamber system.

Thus, a medical device and associated methods for performing morphology-based heart rhythm detection have been presented in the foregoing description with reference to specific embodiments. It is appreciated that various modifications to the referenced embodiments may be made without departing from the scope of the invention as set forth in the following claims.

The invention claimed is:

1. A method, comprising:
sensing a cardiac electrogram (EGM) signal, comprising cardiac depolarization signals, along a plurality of sensing vectors;
sampling the EGM signal over a processing window having a predetermined time duration;
determining a plurality of morphology metrics and associated weighting factors from the sampled EGM signal, a morphology metric of the plurality of morphology metrics having a first weighting factor associating a first sensing vector of the plurality of sensing vectors and a second weighting factor, different from the first weighting factor, associated with a second sensing vector of the plurality of sensing vectors different from the first sensing vector;
updating a value of a rhythm counter based on the associated weighting factors; and
classifying a heart rhythm in response to the updated value of the rhythm counter, the heart rhythm being detected without determining intervals between the cardiac depolarization signals.

2. The method according to claim 1 wherein determining the plurality of morphology metrics comprises determining a slope signal by computing a difference between a plurality of pairs of EGM signal samples.

3. The method according to claim 2 wherein determining the plurality of morphology metrics further comprises determining a low slope content.

4. The method according to claim 2 wherein the slope signal comprises multiple signal peaks corresponding to multiple cardiac depolarizations occurring during the processing window and wherein determining the plurality of morphology metrics further comprises determining a number of signal peaks occurring during the processing window.

5. The method according to claim 1 wherein the EGM signal comprises multiple peaks corresponding to multiple cardiac depolarization signals occurring during the processing window and wherein determining the plurality of morphology metrics comprises aligning the multiple peaks and determining a template corresponding to the aligned multiple peaks.

6. The method according to claim 5 wherein determining the plurality of morphology metrics further comprises comparing each of the multiple peaks to the template.

7. The method according to claim 1 wherein detecting the heart rhythm comprises comparing a morphology metric of the plurality of morphology metrics to a threshold requirement corresponding to a first heart rhythm and increasing a first rhythm counter corresponding to the first heart rhythm in response to the morphology metric meeting the threshold requirement.

8. The method according to claim 7 wherein detecting the heart rhythm further comprises:
increasing a second rhythm counter corresponding to a second heart rhythm in response to the morphology metric not meeting the threshold requirement corresponding to the first heart rhythm;
comparing the first rhythm counter to the second rhythm counter; and
detecting the heart rhythm in response to the comparing of the first rhythm counter and the second rhythm counter.

9. The method according to claim 8 wherein detecting the heart rhythm further comprises comparing a second of the plurality of morphology metrics to a second threshold requirement in response to the first rhythm counter and the second rhythm counter being equal.

10. A non-transitory computer-readable medium having computer-executable instructions for performing a method comprising:
sensing a cardiac electrogram (EGM) signal, comprising cardiac depolarization signals, along a plurality of sensing vectors;
sampling an EGM signal over a processing window having a predetermined time duration;
determining a plurality of morphology metrics and associated weighting factors from the sampled EGM signal, a morphology metric of the plurality of morphology metrics having a first weighting factor associating a first sensing vector of the plurality of sensing vectors and a second weighting factor, different from the first weighting factor, associated with a second sensing vector of the plurality of sensing vectors different from the first sensing vector;
updating a value of a rhythm counter based on the associated weighting factors; and
classifying a heart rhythm in response to a value of the updated rhythm counter, the heart rhythm being detected without determining intervals between the cardiac depolarization signals.

11. The non-transitory computer-readable medium according to claim 10 wherein the EGM signal comprises multiple peaks corresponding to multiple cardiac depolarization signals occurring during the processing window and wherein determining the plurality of morphology metrics further comprises aligning the multiple peaks and determining a template corresponding to the aligned multiple peaks.

12. The non-transitory computer-readable medium according to claim 10 wherein detecting the heart rhythm comprises comparing a one of the plurality of morphology metrics to a threshold requirement corresponding to a first heart rhythm and increasing a first rhythm counter corresponding to the first heart rhythm by an increment in response to the morphology metric meeting the threshold requirement.

13. The non-transitory computer-readable medium according to claim 12 wherein detecting the heart rhythm further comprises:

increasing a second rhythm counter corresponding to a second heart rhythm in response to the morphology metric not meeting the threshold requirement corresponding to the first heart rhythm;

comparing the first rhythm counter to the second rhythm counter; and detecting the heart rhythm in response to the comparison of the first rhythm counter and the second rhythm counter.

14. The non-transitory computer-readable medium according to claim 13 wherein detecting the heart rhythm further comprises comparing a second of the plurality of morphology metrics to a second threshold requirement in response to the first rhythm counter and the second rhythm counter being equal.

15. A medical device, comprising:
a plurality of electrodes sensing an EGM signal, comprising cardiac depolarization signals, along a plurality of sensing vectors;
an analog-to-digital convertor for sampling the EGM signal over a processing window having a predetermined time duration;
a digital signal processor for determining a plurality of morphology metrics from the sampled EGM signal; and
a rhythm detection module configured to classify a heart rhythm in response to the morphology metrics, wherein each of the plurality of morphology metrics is associated with a weighting factor, a morphology metric of the plurality of morphology metrics having a first weighting factor associating a first sensing vector of the plurality of sensing vectors and a second weighting factor, different from the first weighting factor, associated with a second sensing vector of the plurality of sensing vectors different from the first sensing vector, wherein a rhythm counter is updated based on the weighting factor, and wherein the heart rhythm classification is based on the weighting factor.

16. The device according to claim 15 wherein determining the plurality of morphology metrics comprises determining a slope signal by computing a difference between a plurality of pairs of EGM signal samples.

17. The device according to claim 16 wherein determining the plurality of morphology metrics further comprises determining a low slope content.

18. The device according to claim 16 wherein the slope signal comprises multiple signal peaks corresponding to multiple cardiac depolarizations occurring during the processing window and wherein determining the plurality of morphology metrics comprises determining a number of signal peaks occurring during the processing window.

19. The device according to claim 16 wherein the EGM signal comprises multiple peaks corresponding to multiple cardiac depolarizations occurring during the processing window and wherein determining the plurality of morphology metrics further comprises aligning the multiple peaks and determine a template corresponding to the aligned multiple peaks.

20. The device according to claim 19 wherein determining the plurality of morphology metrics further comprises comparing each of the multiple peaks to the template.

21. The device according to claim 15 wherein the rhythm detection module comprises a plurality of rhythm counters corresponding to each of a plurality of heart rhythms and wherein detecting the heart rhythm comprises comparing a morphology metric of the plurality of morphology metrics to a threshold requirement corresponding to a first heart rhythm and increasing a first rhythm counter corresponding to the first heart rhythm by an increment in response to the morphology metric meeting the threshold requirement.

22. The device according to claim 21 wherein detecting the heart rhythm further comprises:
increasing a second rhythm counter corresponding to a second heart rhythm in response to the morphology metric not meeting the threshold requirement corresponding to the first heart rhythm;
comparing the first rhythm counter to the second rhythm counter; and
detecting the heart rhythm in response to the comparison of the first rhythm counter and the second rhythm counter.

23. The device according to claim 22 wherein detecting the heart rhythm further comprises comparing a second of the plurality of morphology metrics to a second threshold requirement in response to the first rhythm counter and the second rhythm counter being equal.

* * * * *